(12) United States Patent
Kleyman

(10) Patent No.: US 8,343,144 B2
(45) Date of Patent: Jan. 1, 2013

(54) APPARATUS AND METHOD FOR VESSEL SEALING AND TISSUE COAGULATION

(75) Inventor: Gennady Kleyman, Brooklyn, NY (US)

(73) Assignee: Expandoheat, LLC, Atlantic Highlands, NJ (US)

( * ) Notice: Subject to any disclaimer, the term of this patent is extended or adjusted under 35 U.S.C. 154(b) by 741 days.

(21) Appl. No.: 12/369,366

(22) Filed: Feb. 11, 2009

(65) Prior Publication Data

US 2009/0204112 A1    Aug. 13, 2009

Related U.S. Application Data

(60) Provisional application No. 61/027,546, filed on Feb. 11, 2008.

(51) Int. Cl.
*A61B 18/04* (2006.01)
(52) U.S. Cl. ......................................................... 606/33
(58) Field of Classification Search .................... 604/33; 606/33, 41; 607/100, 101
See application file for complete search history.

(56) References Cited

U.S. PATENT DOCUMENTS

| | | | | |
|---|---|---|---|---|
| 4,315,510 | A * | 2/1982 | Kihn | 606/33 |
| 4,492,231 | A * | 1/1985 | Auth | 606/42 |
| 4,597,379 | A * | 7/1986 | Kihn et al. | 606/40 |
| 4,869,248 | A | 9/1989 | Narula | |
| 5,151,102 | A * | 9/1992 | Kamiyama et al. | 606/51 |
| 5,383,917 | A * | 1/1995 | Desai et al. | 607/102 |
| 5,462,546 | A | 10/1995 | Rydell | |
| 5,474,530 | A | 12/1995 | Passafaro et al. | |
| 5,527,313 | A | 6/1996 | Scott et al. | |
| 5,528,006 | A | 6/1996 | Gonin et al. | |
| 5,542,916 | A * | 8/1996 | Hirsch et al. | 604/22 |
| 5,571,088 | A | 11/1996 | Lennox et al. | |
| 5,575,772 | A | 11/1996 | Lennox | |
| 5,653,692 | A | 8/1997 | Masterson | |
| 5,697,925 | A | 12/1997 | Taylor | |
| 5,800,493 | A | 9/1998 | Stevens | |
| 5,837,001 | A * | 11/1998 | Mackey | 607/102 |
| 5,843,144 | A | 12/1998 | Rudie et al. | |
| 5,902,251 | A | 5/1999 | van Hooydonk | |
| 6,030,384 | A | 2/2000 | Nezhat | |
| 6,041,260 | A | 3/2000 | Stern et al. | |
| 6,224,593 | B1 * | 5/2001 | Ryan et al. | 606/41 |
| 6,366,818 | B1 | 4/2002 | Bolmsjo | |
| 6,398,779 | B1 * | 6/2002 | Buysse et al. | 606/34 |
| 6,443,947 | B1 | 9/2002 | Marko | |
| 6,447,505 | B2 | 9/2002 | McGovern et al. | |
| 6,635,056 | B2 * | 10/2003 | Kadhiresan et al. | 606/34 |
| 6,730,078 | B2 * | 5/2004 | Simpson et al. | 606/34 |

(Continued)

OTHER PUBLICATIONS

Elastomeric EMI Shielding Solutions, Laird Technologies, pp. 1-11, 21, from www.lairdtech.thomasnet.com/category/thermal?.

(Continued)

*Primary Examiner* — Nicholas Lucchesi
*Assistant Examiner* — Diva K Chander

(57) ABSTRACT

Disclosed is a working end of a surgical instrument for delivering heat energy to tissue. The working end includes paired first and second jaw members movable between open and closed positions, with each jaw member defining a jaw body and jaw end-effecter for engaging and heating tissue. At least one jaw member contains an electromagnetic-energy emitter coupled to an electromagnetic-energy source, the electromagnetic-energy emitter is located within the jaw end-effecter, and the jaw end-effecter includes an insert made of an electromagnetic-energy absorbing material.

17 Claims, 3 Drawing Sheets

U.S. PATENT DOCUMENTS

| | | |
|---|---|---|
| 6,887,240 B1 | 5/2005 | Lands et al. |
| 6,926,716 B2 * | 8/2005 | Baker et al. ................... 606/51 |
| 6,936,047 B2 * | 8/2005 | Nasab et al. ................... 606/34 |
| 7,147,638 B2 * | 12/2006 | Chapman et al. ............... 606/51 |
| 7,278,991 B2 * | 10/2007 | Morris et al. .................. 606/41 |
| 7,419,487 B2 * | 9/2008 | Johnson et al. ................ 606/41 |
| 7,945,332 B2 * | 5/2011 | Schechter ...................... 607/50 |
| 7,955,331 B2 * | 6/2011 | Truckai et al. ................. 606/51 |
| 2003/0199862 A1 * | 10/2003 | Simpson et al. ............... 606/34 |
| 2004/0116979 A1 * | 6/2004 | Truckai et al. ................. 607/51 |
| 2005/0004570 A1 * | 1/2005 | Chapman et al. .............. 606/51 |
| 2005/0033278 A1 * | 2/2005 | McClurken et al. ........... 606/41 |
| 2007/0049914 A1 * | 3/2007 | Eggleston ...................... 606/32 |
| 2007/0219546 A1 * | 9/2007 | Mody et al. .................... 606/27 |
| 2007/0225697 A1 * | 9/2007 | Shroff et al. ................... 606/33 |
| 2010/0094271 A1 * | 4/2010 | Ward et al. .................... 606/33 |

OTHER PUBLICATIONS

PCT /ISA/237 Written Opinion of the Int'l Searching Authority in PCT US2007/024399 (5 pp), Apr. 28, 2008.

* cited by examiner

APPARATUS AND METHOD FOR VESSEL SEALING AND TISSUE COAGULATION

PRIORITY

This application claims priority to U.S. patent application Ser. No. 61/027,546 filed with the U.S. Patent and Trademark Office on Feb. 11, 2008, the contents of which is incorporated herein by reference.

BACKGROUND OF THE INVENTION

The present invention relates to surgical instruments of jaw-structure and methods for sealing of vessels and tissues, and for welding and coagulation of tissues by utilizing electromagnetic energy.

Conventional open and laparoscopic procedures typically involve sealing of vessels and tissues, as well as for welding and coagulation of tissues. Conventional devices apply electromagnetic energy in microwave or radio frequency range directly to the vessels or tissues. As used herein, "microwave frequency range" refers to frequencies between 30 MHz and 30,000 MHz inclusive, where MHz is one million Hertz, and the term "radio-frequency range" refers herein to frequencies between 30 kHz and 30 MHz, where kHz is one thousand Hertz.

A preferred method of tissue-sealing in prior art relies on capturing the tissue in a jaw-structured instrument and applying electromagnetic energy to the captured tissue to cause thermal effect that results in sealing of the tissue. Various mono-polar and bi-polar radio-frequency (RF) jaw structures have been developed for these purposes, such as presented in U.S. Pat. Nos. 5,462,546; 6,030,384; 5,527,313; 6,926,716; 6,887,240; and 5,528,006, the contents of each of which is incorporated herein by reference.

In conventional systems, the jaw structures that engage opposing sides of the captured tissue volume fail to allow for uniform distribution of heat in the tissue. That is, as the initial amount of RF energy applied to the issue, an associated heating of the tissue surface results and the surface accordingly becomes desiccated and resistant to the additional ohmic heating. The efficiency of the conversion of the RF into heating energy substantially decreases. With such devices, localized tissue desiccation and charring can occur almost instantly as tissue impedance rises. The consequence of such uneven distribution of heat can be non-uniform sealing of the tissue. The typical conventional jaw structure that utilize RF energy can cause further undesirable effects as a result of RF energy propagating laterally from the captured tissue, thus causing unwanted collateral thermal damage.

A conventional jaw structure that utilizes microwave energy (see, e.g., U.S. Pat. No. 6,224,593, the contents of which is incorporated herein by reference), apply this energy directly to the treated tissue. Since it is difficult to control the depth of the microwave energy propagation in the tissue, as well as the increase of the temperature in a particular area of the tissue, which causes non-uniform sealing of the tissue and unwanted thermal damage to the unwanted tissue.

The disadvantages of conventional devices make it desirable to provide a jaw structure for vessels and tissue sealing that is powered by an electromagnetic energy source to transmit energy to minimize a period of time necessary for reaching the desired temperature.

It is also further desirable to provide a jaw structure for vessel and tissue sealing configured with selective electro-magnetically-energy-absorbing areas to target sealing areas while minimizing heat exposure to unwanted tissue.

It is therefore desirable to provide a jaw structure for vessel and biological tissue sealing that allows for a relatively brief treatment in a safe and target-oriented manner.

Accordingly, the present invention addresses at least the above-described problems and/or disadvantages and provides at least the advantages described below. An aspect of the present invention provides a jaw structure and method for vessel and tissue sealing, as well as tissue welding and coagulation.

SUMMARY OF THE INVENTION

An aspect of the present invention addresses at least the problems and/or disadvantages and provides at least the advantages described below. Accordingly, an aspect of the present invention provides a jaw structure configured with an antenna or applicator, for the delivery of electromagnetic energy in microwave range to a jaw structure, in which the portion of the jaw structure that is made out of the material impregnated with particles or fillers that absorb electromagnetic energy. During the process of absorption of the electromagnetic energy, the energy is transferred into heat. The generated heat is applied to the treated tissue by means of capturing the tissue in the jaw structure and applying pressure on the tissue, thus causing, depending on the used medical procedure, the sealing of the tissue or vessels, or welding and coagulation of the tissue.

BRIEF DESCRIPTION OF THE DRAWINGS

The above and other features and advantages of exemplary embodiments of the present invention will be more apparent from the following detailed description taken in conjunction with the accompanying drawings, in which.

DETAILED DESCRIPTION OF THE PREFERRED EMBODIMENTS

Figure 1:
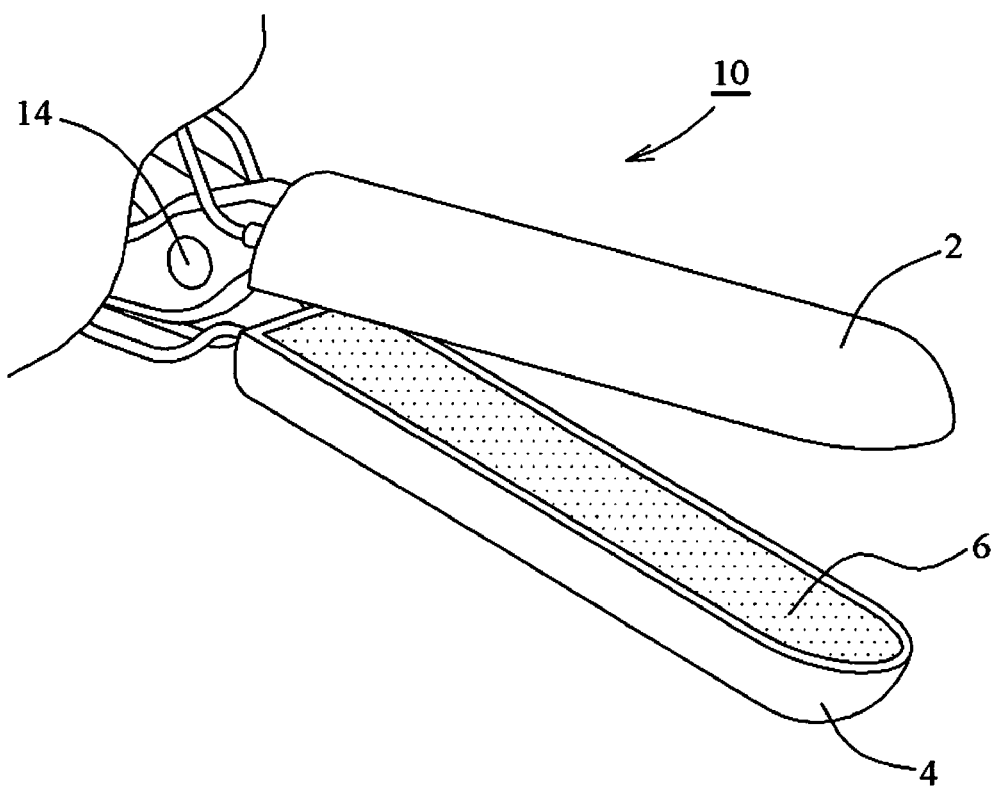
FIG. 1 is a perspective view of an apparatus in accordance with a preferred embodiment of the invention, in an open state.

Reference will now be made in detail to several views of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity, directional terms, such as rear and front may be used with respect to the drawings. These and similar directional terms should not be construed to limit the scope of the invention in any manner. The term "microwave frequency range" refers herein to frequencies between 30 MHz and 30,000 MHz inclusive, where MHz is one million Hertz, and the term "radio-frequency range" refers herein to frequencies between 30 kHz and 30 MHz, where kHz is one thousand Hertz. Although the following description operates via a microwave energy emitter, the present invention is operable by various electromagnetic energy sources and is not limited to microwave energy.

The energy absorbing part of the jaw structure is preferably made from microwave absorbing material by means of extrusion, injection molding or machining. The external portion of the structure is preferably made from a metal and shaped to direct the microwave energy towards the area of the structure, which is made from microwave absorbing material, which in certain embodiments directly contacts the treated tissue and in other embodiments interposes a thin layer of silicone between the microwave absorbing material and the treated tissue.

The jaw structure is further preferably equipped with temperature sensors to control the amount of heat generated in the energy-absorbing portion of the jaw structure, which transfers the heat to treated tissue, thus insuring the proper sealing of the tissue and minimizing the heat exposure to unwanted tissue.

Figure 2:
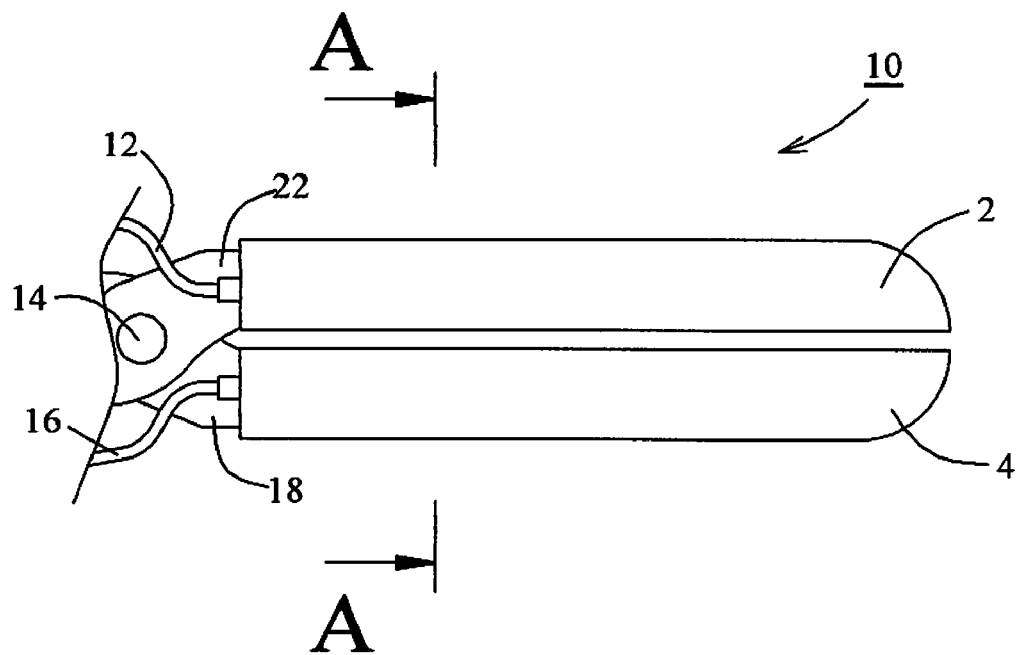
FIG. 2 is a side view of the apparatus of FIG. 1, in a closed state.
Figure 3:
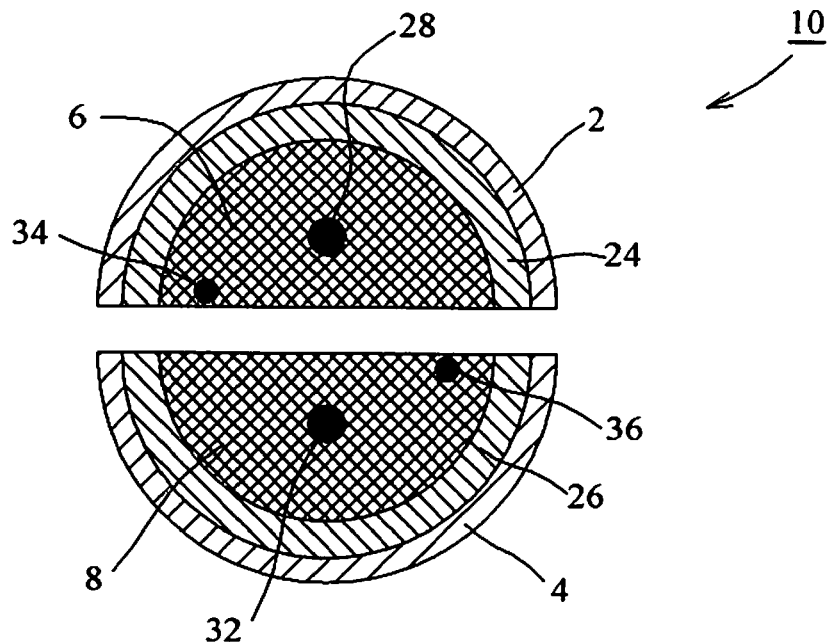
FIG. 3-6 are cross-sectional views of embodiments of the apparatus taken along line A-A on FIG. 2.
Figure 4:
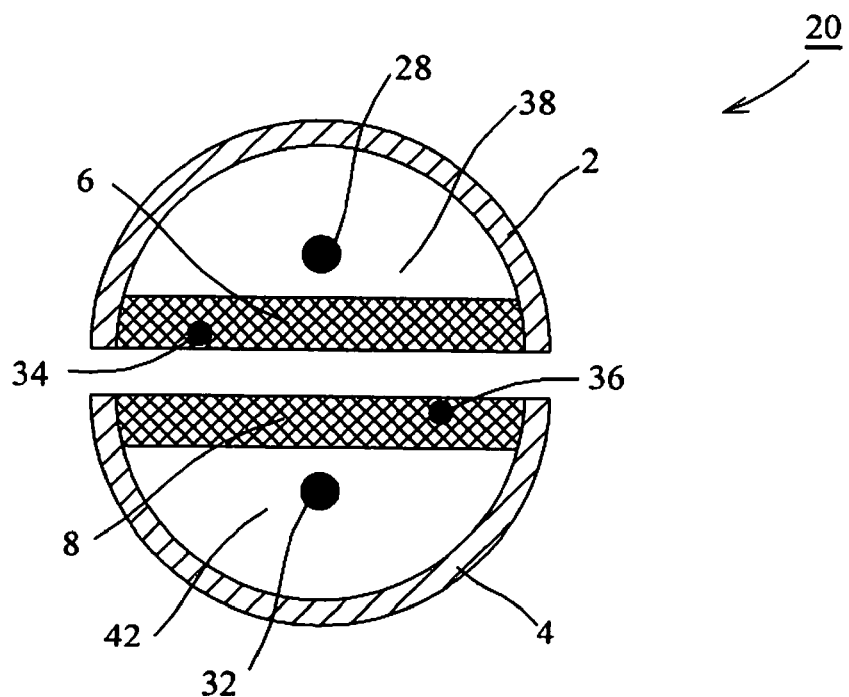
Figure 5:
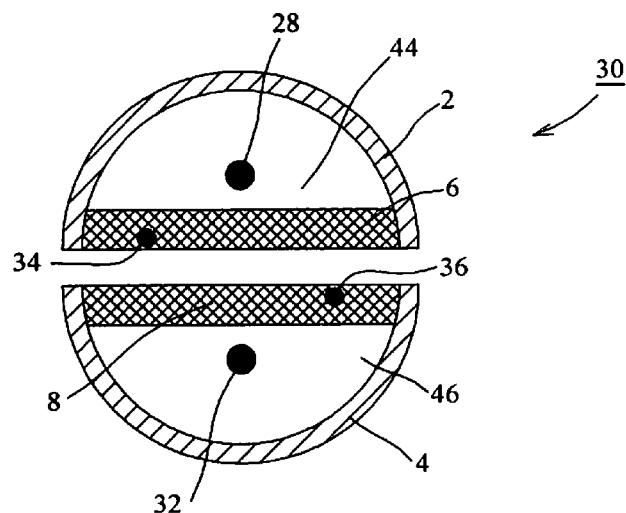
Figure 6:
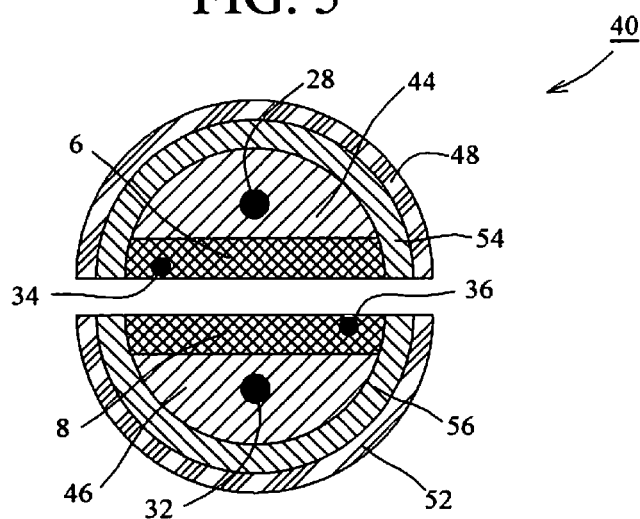
Figure 7:
FIG. 7 is a schematic view of power supply and control systems.

In the associated figures, which set forth other features and advantages of exemplary embodiments of the present invention, FIGS. 1 and 2 are perspective and side views, respectively, of a jaw structure of the present invention; FIG. 3 is a cross-sectional view of the first embodiment of the jaw structure along lines A-A on FIG. 2; FIG. 4 is a cross-sectional view of another embodiment of the present invention taken along lines A-A on FIG. 2; FIG. 5 is a cross-sectional view of further embodiment of the jaw structure along lines A-A on FIG. 2; FIG. 6 is a cross-sectional view of still another embodiment of the jaw structure along lines A-A on FIG. 2; and FIG. 7 is a schematic view of the power supply and control systems.

As shown in the figures, upper and lower jaw bodies 2 and 4 include microwave energy absorbing inserts 6 and 8, and power cords 12 and 14 transfer microwave energy from the power source. A jaw hinge 14 is associated to links 18 and 22 to close and open the jaw bodies 2 and 4 by rotating around the hinge 14. Thermo-isolating inserts 24 and 26 and microwave antennas 28 and 32 (see FIG. 3, et seq.) are also preferably provided. Temperature sensors 34 and 36 as well as air gaps 38 and 42 coexist with non-metal, non-energy absorbing inserts 44 and 46, preferably further provided for structural integrity. Non-metal outer shells 48 and 52 correspond to metal inserts for microwave reflection and concentration and structural integrity 54 and 56.

While the invention has been shown and described with reference to exemplary embodiments thereof, it will be understood by those skilled in the art that various changes in form and details may be made therein without departing from the spirit and scope of the invention, as defined by the following claims.

What is claimed is:

1. An apparatus for use as a working end of a surgical instrument, the apparatus comprising:
   paired first and second jaw members movable between open and closed positions; and
   an electromagnetic-energy emitter contained within at least one jaw member; and
   an electromagnetic-energy absorbing insert at least partially disposed between said electromagnetic-energy emitter and tissue retained between said paired jaw members,
      wherein the emitter is coupled to an electromagnetic-energy source for delivery of electromagnetic-energy to said electromagnetic-energy absorbing insert to be absorbed and transfers as heat energy to said tissue, and the electromagnetic-energy emitter is positioned within a jaw end-effecter.

2. The apparatus of claim 1, wherein the inserts absorb electromagnetic energy in microwave region.

3. The apparatus of claim 1, wherein the jaw body of the jaw members is made of electromagnetic energy reflecting material.

4. The apparatus of claim 3, wherein the jaw body reflects electromagnetic energy in the microwave region.

5. The apparatus of claim 1, wherein the electromagnetic-energy absorbing insert is formed of a material that includes a plurality of particles that absorb electromagnetic energy.

6. The apparatus of claim 5, wherein the plurality of particles are formed of materials including nickel, silver, aluminum, nickel-plated graphite, silver-plated aluminum, silver plated copper, silver-plated nickel, silver-plated glass and a combination thereof.

7. The apparatus of claim 1, wherein an external surface of the jaw end-effecter is coated with biocompatible material un-reactive to the tissue.

8. The apparatus of claim 7, wherein the biocompatible material is silicone.

9. The apparatus of claim 1, further comprising a sensor to monitor temperature of the jaw end-effecter for engaging and heating tissue.

10. The apparatus of claim 1, wherein first and second electromagnetic-energy emitters are provided in first and second jaw members, respectively, each having an insert made of electromagnetic-energy absorbing material and each jaw member being made of an electromagnetic-energy reflecting material.

11. The apparatus of claim 10, wherein the electromagnetic-energy reflecting material is one of stainless steel, copper and aluminum.

12. The apparatus of claim 1, further comprising a jaw body shaped to direct the reflected electromagnetic energy toward the insert.

13. The apparatus of claim 12, wherein the emitter is located inside the insert.

14. The apparatus of claim 12, wherein the emitter is located between the insert and jaw body.

15. The apparatus of claim 14, further comprising a space made of heat-insulating material separating the insert and jaw body.

16. A method for working an end of a surgical instrument, the method comprising:
   moving paired first and second jaw members between open and closed positions having an electromagnetic-energy emitter contained within at least one jaw member; and
   delivering, from the emitter coupled to an electromagnetic-energy source, heat energy to tissue, wherein the emitter positioned within a jaw end-effecter includes an electromagnetic-energy absorbing insert.

17. The method of claim 16, wherein said delivering comprises
   receiving electromagnetic-energy from said emitter into said electromagnetic-energy absorbing insert, and
   transferring heat energy to said tissue by said electromagnetic-energy absorbing insert in response to electromagnetic energy received from said emitter, said electromagnetic-energy absorbing insert being disposed between said emitter and said tissue.

* * * * *